(12) United States Patent
Gobius Du Sart et al.

(10) Patent No.: US 10,578,549 B2
(45) Date of Patent: Mar. 3, 2020

(54) QUANTIFICATION OF LACTIDE AMOUNTS IN A POLYMERIC MATRIX

(71) Applicant: PURAC BIOCHEM BV, Gorinchem (NL)

(72) Inventors: Gerrit Gobius Du Sart, Herwijnen (NL); Vincent De Jong, Gorinchem (NL); Jan Arie Niessen, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 14/406,638

(22) PCT Filed: Jun. 7, 2013

(86) PCT No.: PCT/NL2013/050408
§ 371 (c)(1),
(2) Date: Dec. 9, 2014

(87) PCT Pub. No.: WO2013/187758
PCT Pub. Date: Dec. 19, 2013

(65) Prior Publication Data
US 2015/0168295 A1    Jun. 18, 2015

(30) Foreign Application Priority Data
Jun. 11, 2012    (NL) .................................... 1039667

(51) Int. Cl.
*G01N 21/3563*    (2014.01)
*G01N 21/359*    (2014.01)
(Continued)

(52) U.S. Cl.
CPC ......... *G01N 21/3563* (2013.01); *C08G 63/08* (2013.01); *C08L 67/04* (2013.01);
(Continued)

(58) Field of Classification Search
CPC ..... G01N 2201/0861; G01N 2201/061; G01N 21/359; G01N 21/3563
(Continued)

(56) References Cited

U.S. PATENT DOCUMENTS 2,758,987 A * 8/1956 Salzberg .............. C08G 63/823
528/354
4,281,645 A * 8/1981 Jobsis .................. A61B 5/0059
600/324
(Continued)

FOREIGN PATENT DOCUMENTS

| EP | 0762109 A2 | 3/1997 |
| EP | 0762109 A3 | 9/1997 |
| JP | 2011173844 A | 9/2011 |

OTHER PUBLICATIONS

Lasprilla et al. (Synthesis and Characterixzatioin of Pll (Lactic Acid) for Use in Biomedical Field, Chemical Engineering Transactions 24:985 Jan. 2011).*
(Continued)

*Primary Examiner* — David P Porta
*Assistant Examiner* — Djura Malevic
(74) *Attorney, Agent, or Firm* — Oliff PLC

(57) ABSTRACT

The present invention relates to a method for quantification of the amount of lactide in a lactide-based polymeric matrix by means of Infra Red Spectroscopy measurement. According to the invention the quantification is based on measurements performed on absorptions in the near Infra Red region of the electromagnetic spectrum. The invented method allows a rapid, easy and cheap quantification of lactide in a polymeric matrix, especially in PLA.

8 Claims, 6 Drawing Sheets

Figure 2:
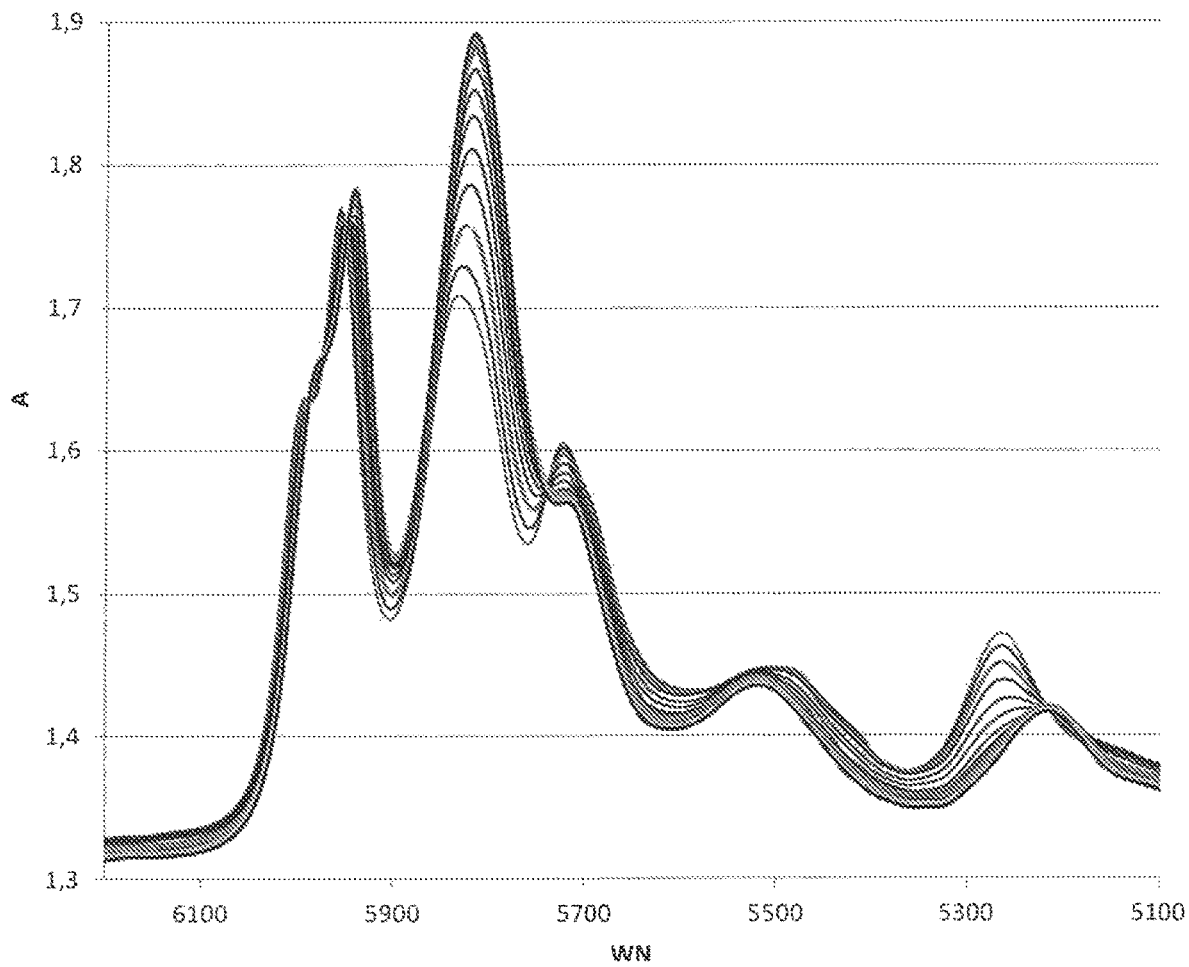

(51) Int. Cl.
 *C08L 67/04* (2006.01)
 *C08G 63/08* (2006.01)
 *G01N 21/84* (2006.01)
 *G01N 21/3577* (2014.01)

(52) U.S. Cl.
 CPC ....... *G01N 21/359* (2013.01); *G01N 21/3577* (2013.01); *G01N 2021/8411* (2013.01); *G01N 2021/8416* (2013.01); *G01N 2201/061* (2013.01); *G01N 2201/0826* (2013.01)

(58) Field of Classification Search
 USPC .................................................... 250/339.07
 See application file for complete search history.

(56) References Cited

U.S. PATENT DOCUMENTS

| | | | | |
|---|---|---|---|---|
| 4,505,583 A * | 3/1985 | Konomi | ............. | A61B 1/00165 356/417 |
| 4,805,623 A * | 2/1989 | Jobsis | ................ | A61B 5/14551 250/339.12 |
| 5,194,473 A * | 3/1993 | Shinoda | ................... | A61L 17/12 524/263 |
| 5,361,758 A * | 11/1994 | Hall | ................... | A61B 5/14532 600/322 |
| 5,379,764 A * | 1/1995 | Barnes | ............... | A61B 5/14532 250/339.11 |
| 5,433,197 A * | 7/1995 | Stark | ................... | A61B 5/14532 600/316 |
| 5,435,309 A * | 7/1995 | Thomas | ............. | A61B 5/14532 250/339.12 |
| 5,441,054 A * | 8/1995 | Tsuchiya | .............. | A61B 5/0059 250/341.1 |
| 5,442,032 A * | 8/1995 | Arnold | ................. | A61L 17/105 428/357 |
| 5,459,317 A * | 10/1995 | Small | ................ | A61B 5/14532 250/341.1 |
| 5,757,002 A * | 5/1998 | Yamasaki | ............ | A61B 5/1455 250/339.12 |
| 5,986,331 A * | 11/1999 | Letavic | ................... | H01L 23/66 257/347 |
| 6,166,169 A * | 12/2000 | Fritz | .................... | C08G 63/823 528/176 |
| 7,212,077 B2 * | 5/2007 | Schilling | .............. | H01Q 13/206 333/109 |
| 7,298,234 B2 * | 11/2007 | Dutta | .................... | H01P 1/2005 333/236 |
| 7,626,476 B2 * | 12/2009 | Kim | ....................... | H01P 3/003 333/238 |
| 7,695,795 B1 * | 4/2010 | Smith | ................ | C08G 63/6822 428/364 |
| 7,723,461 B1 * | 5/2010 | Wagener | ................ | C08G 63/00 525/450 |
| 7,754,826 B1 * | 7/2010 | Smith, Jr. | .............. | C08G 63/08 525/450 |
| 7,776,359 B1 * | 8/2010 | Hennink | .............. | A61K 9/0019 424/426 |
| 7,896,498 B2 * | 3/2011 | Munger | ................ | A61B 5/0066 351/213 |
| 8,344,042 B2 * | 1/2013 | Liu | ..................... | A61L 27/3821 424/422 |
| 8,818,477 B2 * | 8/2014 | Soller | ................ | A61B 5/14551 600/317 |
| 9,234,887 B2 * | 1/2016 | Bramanti | ......... | G01N 33/48707 |
| 9,924,901 B2 * | 3/2018 | Guthrie | .............. | A61B 5/14546 |
| 2005/0222379 A1 | 10/2005 | Matsuo et al. | | |
| 2008/0154101 A1 * | 6/2008 | Jain | ...................... | A61B 5/0017 600/309 |
| 2010/0141359 A1 * | 6/2010 | Tzuang | .................. | H01P 3/088 333/238 |
| 2010/0256746 A1 * | 10/2010 | Taylor | .................. | A61K 31/435 623/1.42 |
| 2010/0256748 A1 * | 10/2010 | Taylor | .................... | A61L 31/10 623/1.46 |
| 2011/0038936 A1 * | 2/2011 | Griswold | ............. | A61K 9/0092 424/486 |
| 2011/0064652 A1 * | 3/2011 | Borlak | ................... | A61K 9/007 424/1.11 |
| 2012/0040015 A1 * | 2/2012 | Lehtonen | ............... | A61L 27/446 424/602 |

OTHER PUBLICATIONS

Rohman et al., "Design of Porous Polymeric Materials from Interpenetrating Polymer Networks (IPNs): Poly(DL-lactide)/Poly(methyl methacrylate)-Based Semi-IPN Systems," Macromolecules, Jan. 2005, vol. 38, No. 17, pp. 7274-7285.

Braun et al., "Infrared Spectroscopic Determinationn of Lactide Concentration in Polyactide: An Improved Methodology," Macromolecules, Dec. 2006, vol. 39, No. 26, pp. 9302-9310.

Thosar et al., "Determination of copolymer ratios of poly(lactide-co-glycolide) using near-infrared spectroscopy," Journal of Pharmaceutical and Biomedical Analysis, Jun. 1999, vol. 20, pp. 107-114.

Jul. 25, 2013 Written Opinion issed in International Application No. PCT/NL2013/050408.

Jul. 25, 2013 International Search Report issued in International Application No. PCT/NL2013/050408.

Apr. 25, 2016 Office Action issued in Eurasian Application No. 201492033/28.

Nov. 16, 2017 Office Action issued in Chinese Application No. 201380037692.0.

Apr. 18, 2019 Office Action issued in European Application No. 13 732 648.4.

* cited by examiner

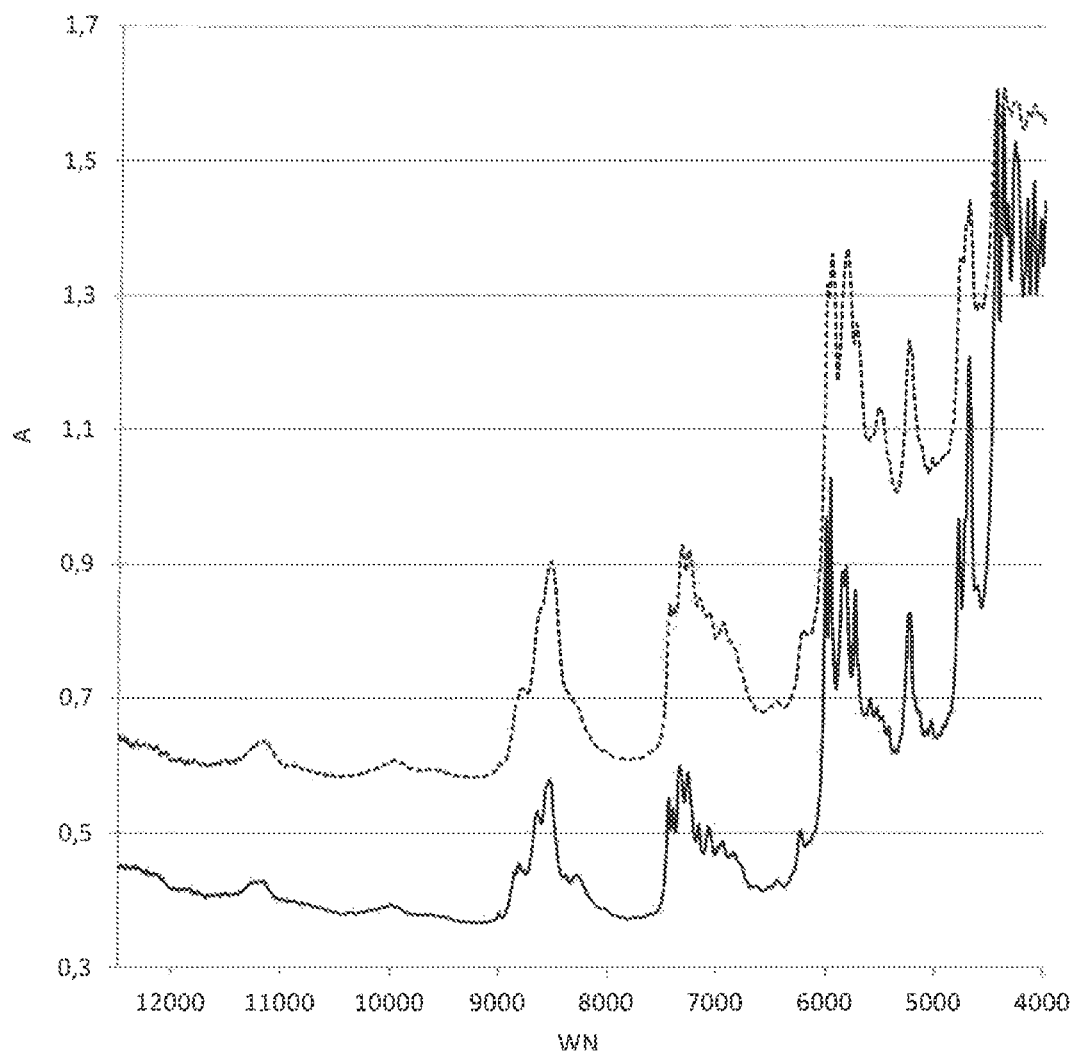
FIGURE 1-A

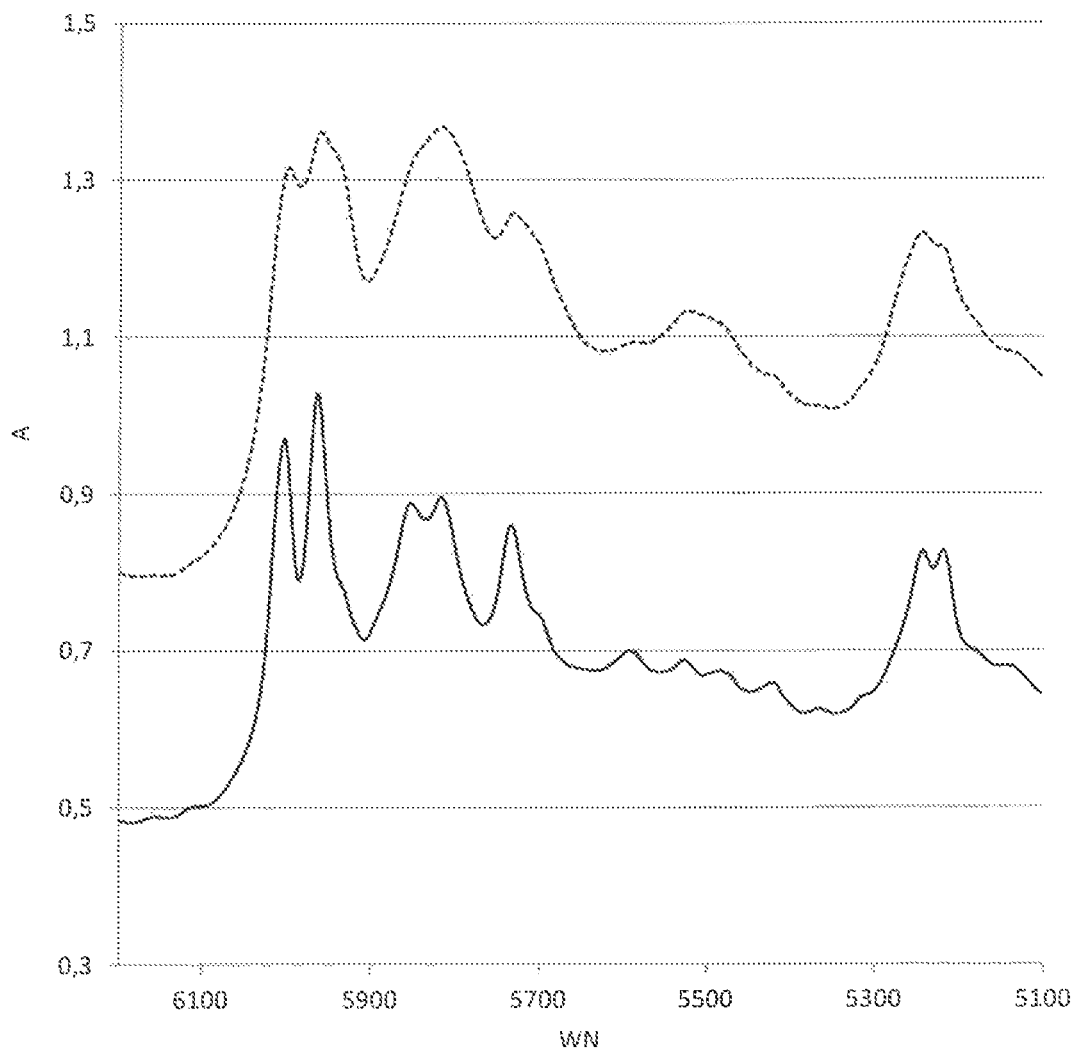
FIGURE 1-B

QUANTIFICATION OF LACTIDE AMOUNTS IN A POLYMERIC MATRIX

The present invention relates to a method for quantification of the amount of lactide in a lactide-based polymeric matrix by means of Infra Red Spectroscopy measurements.

Lactide is a well-known intermediate product in the manufacturing of polymer materials, like polylactic acid (PLA) or PLA-containing copolymers. Lactide (sometimes called dilactide) is a cyclic dimer of lactic acid. Lactide is usually manufactured by means of a two-step process. In the first step, lactic acid is polymerized into a so-called pre-polymer of relatively low molecular weight. In the second step, crude lactide is formed from this pre-polymer by means of a so-called 'backbiting' process in the presence of a catalyst. This crude lactide material can be purified and subsequently be used in a polymerization process to manufacture PLA or PLA-containing copolymers.

It is well-known that lactide can exist in three different geometric structures, which have a diastereomeric relationship. These different structures can be distinguished as R,R-lactide (or D-lactide), S,S-lactide (or L-lactide) and R,S-lactide (or meso-lactide). Mixtures of equal amounts of D- and L-lactide are often referred to as racemic lactide or rac-lactide. Within the scope of the present invention, both the three pure lactides (being composed of only one diastereomer) as well as mixtures of two or more of the pure lactides can be used.

A method of the type mentioned in the opening paragraph is known as such, for example from a publication in Macromolecules Vol 39, No 26, pages 9302-9310 (2006). More in detail, this publication discloses a new Fourier transform Infra Red spectroscopy method for measuring lactide concentrations in a PLA matrix. In this method, mid Infra Red absorptions originating from a specific ring vibration of lactide and absorptions originating from the methyl vibration of both lactide and PLA are used to quantify the lactide concentration in the polymeric matrix, which is substantially composed of PLA.

The known method has several disadvantages. First, the present inventors have some doubts about the accuracy of the method in the measurements of low lactide concentrations, and especially of concentrations below 1% by weight. Secondly, the known method can only be applied with equipment, which is unpractical for use in industrial circumstances. This concerns especially the set-up needed for measurements of the described type, which necessitates the aligning of sensitive mirrors arrays in vacuum tubes and a complicated probe design.

In Applicants view, there exists a strong need to simplify the lactide quantification method as described in the mentioned publication. More specifically, Applicants want to provide an accurate yet simple, flexible and cost-effective lactide quantification method, which does not require a complicated experimental set-up. Such quantification method should preferably be operable in various stages of a lactide production process and of a process in which lactide is converted into a polymer material, like PLA or PLA-containing polymers.

These and other objects of the present invention are achieved by means of a method for quantification of the amount of lactide in a lactide-based polymeric matrix by means of Infra Red Spectroscopy measurements, which method is further characterized according to the present invention, in that the quantification is based on measurements performed on absorptions in the near Infra Red region of the electromagnetic spectrum.

The invention is based on the experimentally obtained insight of the inventors that, contrary to popular belief, very small amounts of lactide can be measured and quantified in a matrix of polymer materials by means of near Infra Red (nIR) measurements. By using this method amounts of lactide as small as 0.1% by weight in a polymeric matrix can be quantified in an accurate and reproducible manner. The invented method appears to be much more accurate as compared with equipment designed for mid Infra Red measurements. Moreover, the handling for performing the nIR measurements, like the sample preparation and the data analysis, is less time-consuming as compared to commonly used off-line methods based on Gas Chromatography (GC) or Liquid Chromatography (LC). In latter off-line methods, dissolving the polymer matrix can take up to 24 hrs. This means that such off-line methods are not suited for process control purposes.

It is noted that in practice the nIR spectrum is defined to range from approximately 12000-4000 $cm^{-1}$. In this spectral range, molecular overtone and combination vibrations of lactide appear to be visible. The corresponding absorption peaks are rather broad and overlapping, resulting in complex nIR spectra. In these spectra, the various peaks cannot unambiguously be assigned to specific vibrations. Nevertheless, nIR measurements on well-defined mixtures of lactide and polymer materials surprisingly show that calibration curves with very good fits can be obtained. In can therefore be concluded that very small amounts of lactide in such mixtures can be quantified.

A preferred embodiment of the method according to the present invention is characterized in that the polymeric matrix comprises PLA. As lactide and its polymer product, PLA are structurally strongly related, strong overlapping overtone peaks in the nIR region of both lactide and PLA can be expected. Such overlap would increase with an increasing amount of PLA in the polymeric matrix. The inventors however found that good fitting calibration curves can still be obtained, even in the case that the amount of lactide in PLA is very small. Thus, lactide amounts less than 0.5% by weight based on the total amount of lactide and polymeric matrix can be measured in a reproducible manner. This unexpected finding is interesting as it allows for quantification of lactide in a polymeric matrix which comprises significant amounts of PLA aside to other polymers. So, lactide quantification is possible in co-polymers of PLA with other polymers, especially with polyesters.

Another preferred embodiment of the invented method is characterized in that the polymeric matrix essentially consists of PLA. Such polymeric matrix essentially consisting of PLA is to be understood as a polymeric matrix consisting of at least 90%, preferably at least 95% and more preferably of at least 98% by weight of PLA. It has been found that even in these (almost) pure PLA matrices, small amounts of lactide of 0.1% by weight and even less can still be determined by use of the presently invented quantification method.

Also preferred is the embodiment of the invented method which is characterized in that the PLA has a $M_n$ of at least 10000 kg/mol. In practice this means that the lactide is almost completely polymerized via a ring-opening-polymerization process into PLA. So, it appears that the degree of polymerization of lactide into PLA does not negatively interfere with the accuracy of the quantification results of the lactide amount in the PLA matrix. The (number-averaged) molecular weight ($M_n$) is determined by GPC measurements versus polystyrene standards.

Interesting is also the embodiment which is characterized in that the amount of lactide is measured in the final polymerization product of the polymeric matrix. In the area of PLA (copolymer) manufacture, it is well known that the concentration of lactide in the final polymerization products is an important quality feature of such polymer product. There is a general desire to have and maintain the lactide amounts in these polymer products as low as possible. This holds especially for (almost) pure PLA polymer products. With the present quantification method, such small lactide concentrations can relatively easily be determined and the quality of the final product be ensured.

Much interest is also devoted to a preferred embodiment of the now invented method, which is characterized in that the amount of lactide is measured in a polymerization process in which lactide is polymerized into a lactide based polymeric matrix. The presently invented method allows lactide quantifications in all stages of the lactide to PLA polymerization process in a relatively easy manner. Such measurements can be performed as early as at the start of the polymerization process until the moment at which the polymerization reaction is completed and (optionally) the residual lactide has been removed. In this manner, the lactide-into-PLA conversion process can be monitored, and also controlled, online.

Preferably the polymerization process is designed as a batch process. In this preferred embodiment of the method according to the current invention, the quantification of the amount of lactide can be performed at any desired stage of the polymerization process. It is even possible to monitor the whole reaction, i.e. to continuously quantify the change in lactide concentration from the start of the polymerization reaction until its completion.

Another, more preferred embodiment of the invented lactide quantification method has the feature that the polymerization process is a continuous process. In such continuous process, the amount of lactide can be quantified on certain points of interest in the polymerization equipment. In case of more points of interest, said lactide quantification can be performed by using multiple measuring probes in combination with a single nIR measuring apparatus. The resulting data can be calculated instantaneously and preferably with a single data calculator. So, online monitoring of the conversion of lactide in a continuous lactide-to-PLA polymerization process via ring-opening polymerization is now possible. As a result of the present invention, the process and quality control of such a continuous process has become much simpler. Moreover, undesired deviations occurring during the (polymerization) process can be determined in a very early stage, so that changes in process parameters to repair these deviations can be applied in an early stage. As a result, possible product loss can be minimized.

The invented quantification method can be performed with any state of the art near Infra Red measurement apparatus. Although measurements in the nIR spectral range between 6100 and 5100 cm$^{-1}$ provide most relevant information (first overtones), measurements in a broader nIR range like between 12000 and 4000 cm$^{-1}$ provide more accurate data, as this broader range may include second and higher overtones of lactide. Such nIR apparatus may comprise a measuring chamber, which chamber is provided with a near Infra Red source and a measuring probe. Latter probe may be connected via an optical fiber to the near Infra Red source as well as a software module. An apparatus of this design is especially suitable for online measuring of polymerization processes. Especially preferred is a nIR apparatus which is equipped with a number of probes which are all connected to the near Infra Red source via optical fibers. Such apparatus having two or more probes is especially suitable for use in a continuous lactide-to-PLA process in which the lactide concentration should be simultaneously determined at different stages of the polymerization process.

Compared with the apparatus needed for mid Infra Red measurements of lactide, the apparatus for measuring near IR spectra can be rather simple. Especially neither vacuum parts nor adjustment of mirrors in such vacuum parts are necessary. The simple design of the near IR apparatus needed for performing the lactide quantifications is seen as an attractive aspect of the present invention. In this respect, it is also noted that the range of mid Infra Red signal transport via state of the art optical fibers is rather limited (few meters) due to signal losses. However, near Infra Red signals can be transmitted for hundreds of meters through the same optical fibers without significant losses. So, a single nIR apparatus with several probes connected via optical fibers can be used for monitoring a complete lactide production or lactide conversion plant.

Figure 3:
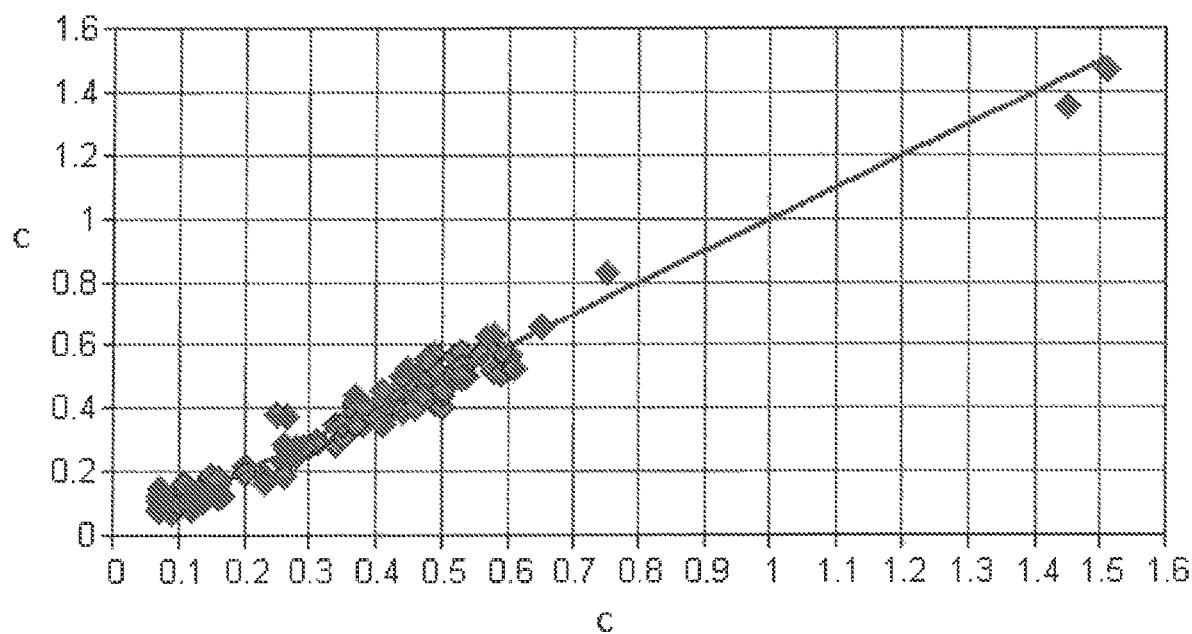
Figure 4:
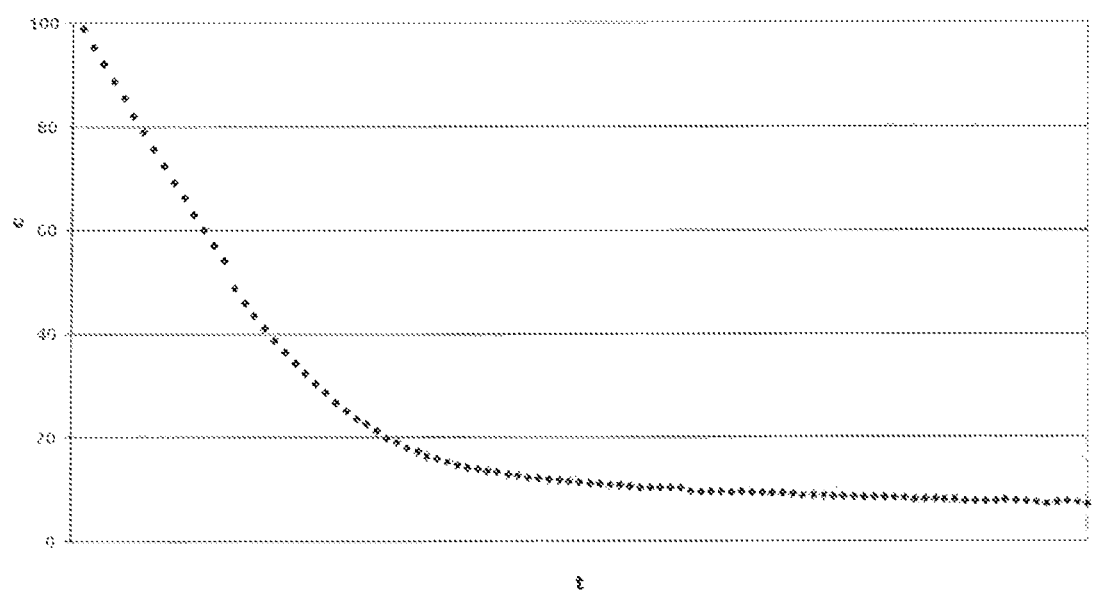
Figure 5:
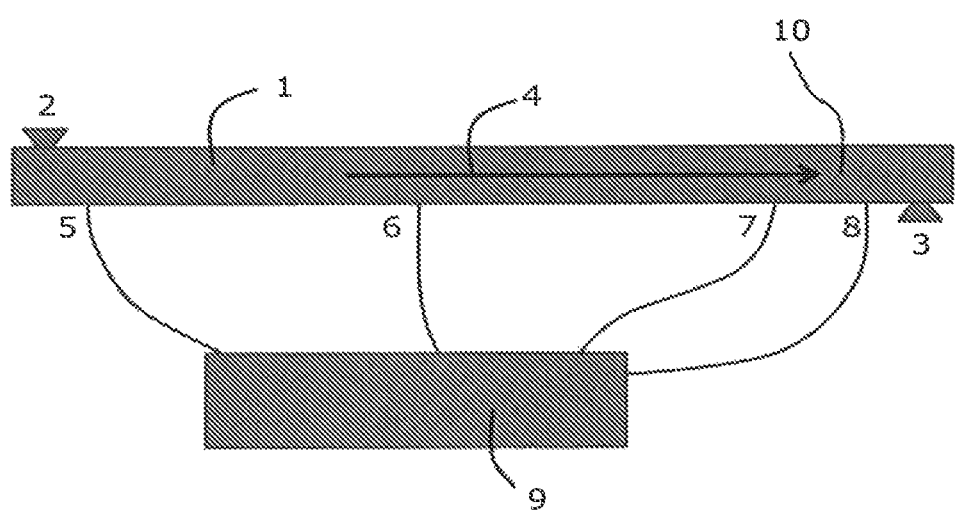

The present invention is described in more detail and elucidated by different examples and a drawing, in which FIG. 1 shows several nIR spectra of lactide, both in the absence and presence of a polymeric matrix, FIG. 2 depicts a series of near IR spectra measured with different concentrations of lactide in a PLA polymeric matrix, FIG. 3 shows a calibration curve of measured and calculated data of lactide concentrations in a PLA matrix, FIG. 4 shows a plot in which the amount of lactide in a lactide-to-PLA polymerization batch process is measured, and FIG. 5 shows a schematic diagram of a continuous lactide-to-PLA polymerization process indicating the points of interest where near Infra Red measurements can be performed In FIGS. 1 and 2, nIR spectra are shown, in which the absorption A is depicted as a function of the wave number WN. In more detail, FIG. 1-A shows nIR spectra of L-lactide (Puralact Polymer Grade), both measured in pure form (solid line, sample 1) and measured in a polymeric matrix (dotted line, sample 2). The spectra were recorded in reflective mode over the range between approximately 12000 and 4000 cm$^{-1}$. Sample 2, having lactide in a polymeric matrix of PLA, contained 48% by weight of L-lactide in 52% by weight of PLA. The $M_n$ of the PLA was higher than 10000 kg/mol. The measurements were performed with a Bruker MPA IR spectrometer. The peaks of interest for the quantification method according to the present invention are located in the spectral range between 6100 and 5100 cm$^{-1}$. FIG. 1-B shows in more detail the spectra of both samples 1 and 2 over this smaller spectral range.

FIG. 2 shows how the near IR spectrum of lactide changes as a result of its conversion into PLA. The conversion started with 100% of weight of lactide and stopped after 52% by weight of the lactide was polymerized into PLA. This polymerization has a notable effect on especially two absorptions. First, the peak around 5830 cm$^{-1}$ appears to increase in time during the polymerization process. Secondly, a decrease and shift is observed of the peak around 5270-5220 cm$^{-1}$. This part of the nIR spectrum can be used to fill the model that will finally enable calculating lactide amounts from observed spectra. Different samples were drawn from the reaction medium and quenched after which the lactide amount was measured by off-line techniques such as Gas Chromatography (GC) or Liquid Chromatography (LC). These lactide amounts are assigned to the relevant spectra when building the calculation model.

FIG. 3 shows a so-called cross-validation curve of measurements of lactide in a polymeric matrix. In order to determine this curve, a series of samples with different concentrations of lactide in a polymeric matrix have been prepared. The amount of lactide was varied between 0.05 and 1.5 wt %. In the present case, PLLA ($M_n$ larger than 10000) was used as the polymeric matrix. The lactide-concentration C' was measured as a function of the known lactide-concentration C in the samples. Based on the cross-validation curve it was concluded that very low amounts of lactide can be reproducibly measured in a lactide-containing polymeric matrix. The root mean square of the error cross validation was shown to be 0.04. This small value allows to measure lactide concentration as low as approximately 0.05% by weight in a reproducible manner by means of the invented method.

FIG. 4 shows a plot of the lactide concentration C which was online quantified by means of the method according to the present invention as a function of time t. In the course of this experiment, 400 g of L-lactide (Puralact Polymer Grade) was added to a reaction vessel, which was heated to 180° C. and the lactide was allowed to melt under continuous stirring. A nIR probe was positioned in the vessel for monitoring the lactide-to-PLA conversion. After the lactide was molten in the vessel, 60 mg of catalyst (Tin-octoate) and 4.12 g of initiator (n-hexanol) were added.

The moment of adding the catalyst and the initiator was chosen as t=0. At that moment, the lactide concentration was 100%. Due to the rapid ring-opening polymerization (ROP) of lactide into PLA, the lactide concentration dropped rapidly after t=0. After 6 min, the lactide concentration reached an equilibrium value of approximately 3%. The small deviations on the line are attributed to the presence of temperature fluctuations within the vessel. These fluctuations are expected due to the temperature sensitivity of molecular vibrations. Incorporation of temperature effects into the model results in a significant improvement in the accuracy of the measurement.

FIG. 5 shows schematically an interesting application of the presently invented quantification method in the course of a continuous process for lactide-to-PLA polymerization. For this purpose, tube reactor 1 is fed at reactor entrance site 2 with lactide. The added lactide is either in the liquid phase or fed as a solid mass, which mass is heated in the tube so that the lactide becomes liquid. An appropriate amount of catalyst (Tin-octoate) and initiator (n-hexanol) is added, either just before the adding of the lactide or just after it was entered at site 2. The entered lactide is transferred by means of pressure through the length of the reactor body to reactor exit site 3 in the direction indicated by arrow 4. During the transfer, the lactide is converted into its polymerization product PLA. Care is taken that the reactor is kept at a temperature at which both lactide and PLA are in the liquid phase.

The tube reactor contains at various locations four probes 5, 6, 7 and 8 for measuring the nIR spectrum of the reaction mixture which is transferred through the reactor. These probes are connected by means of optical fibers to a nIR measuring apparatus 9. In the apparatus, the measured spectra values are converted to amounts of lactide in the polymeric matrix of PLA. This conversion is based on a calculation model that is validated by the use of recorded nIR spectra of reaction mixtures with known amounts of lactide in PLA. Critical measuring points in the reactor are the reactor entrance 2 and the reactor exit 3.

Tube reactor 1 may comprise a devolatilisation unit at location 10 (not shown in detail), which unit is aimed at the removal of unconverted lactide or other (volatile) impurities from the polymer. In such situation, critical measurement points 7 and 8 are preferably located in the tube reactor 1 just before and just after such devolatilisation unit 10.

With the presently invented lactide quantification method, small amounts of lactide can be determined online in a polymeric matrix in a relatively simple manner.

While the invention has been illustrated and described in detail in the foregoing description, such description is to be considered illustrative or exemplary and not restrictive; the invention is not limited to the disclosed embodiments and experiments. Variations to the disclosed embodiments can be understood and effected by those skilled in the art in practicing the claimed invention, from a study of the disclosure and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. Method comprising quantification of the amount of lactide, which is a cyclic dimer of lactic acid, in a lactide-based polymeric matrix by means of Infra Red Spectroscopy measurements,
wherein the amount of lactide is measured in a reaction mixture in which said lactide is polymerized into said lactide based polymeric matrix, which polymeric matrix comprises polylactic acid (PLA) or PLA-containing copolymers,
wherein the quantification is based on measurements performed on absorption spectra recorded by a spectrometer comprising at least one probe disposed in the reaction mixture and operated in the range between 12000 cm$^{-1}$ and 4000 cm$^{-1}$ in the near Infra Red region of the electromagnetic spectrum so as to capture molecular overtones and combination vibrations of said lactide, and
wherein said quantification of the amount of lactide further includes converting said measurements performed on said absorption spectra using a calculation model that is validated by the use of recorded near Infra Red spectra of mixtures having known amounts of lactide in PLA.

2. Method according to claim 1, wherein the polymeric matrix comprises PLA.

3. Method according to claim 2, wherein the polymeric matrix essentially consists of PLA.

4. Method according to claim 2, wherein the PLA has a $M_n$ of at least 10.000 kg/mol.

5. Method according to claim 1, wherein the amount of lactide is measured in the final polymerization product of the polymeric matrix.

6. Method according to claim 1, wherein the polymerization process is a batch process.

7. Method according to claim 1, wherein the polymerization process is a continuous process.

8. Method according to claim 7 wherein the amount of lactide is measured simultaneously at different stages of the polymerization process.

* * * * *